(12) United States Patent
Okano

(10) Patent No.: US 7,902,143 B2
(45) Date of Patent: Mar. 8, 2011

(54) CANCER ANTIGEN PEPTIDE AND THE USE THEREOF

(75) Inventor: Fumiyoshi Okano, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 489 days.

(21) Appl. No.: 11/792,400

(22) PCT Filed: Dec. 6, 2005

(86) PCT No.: PCT/JP2005/022369
§ 371 (c)(1),
(2), (4) Date: Dec. 3, 2007

(87) PCT Pub. No.: WO2006/062094
PCT Pub. Date: Jun. 15, 2006

(65) Prior Publication Data
US 2009/0214480 A1    Aug. 27, 2009

(30) Foreign Application Priority Data

Dec. 7, 2004    (JP) ................................ 2004-353820

(51) Int. Cl.
*A61K 38/00* (2006.01)
*A61K 38/08* (2006.01)
*C07K 7/00* (2006.01)
*C07K 7/06* (2006.01)

(52) U.S. Cl. ....... 514/1.1; 514/19.2; 514/19.3; 514/21.6; 514/21.7; 530/300; 530/328

(58) Field of Classification Search .................. None
See application file for complete search history.

(56) References Cited

U.S. PATENT DOCUMENTS 6,184,204 B1    2/2001    Boots et al.
6,881,824 B1    4/2005    Boots et al.

OTHER PUBLICATIONS

Rudinger J, "Characteristics of the amino acids as components of a peptide hormone sequence," Peptide Hormones, JA Parsons Edition, University Park Press, Jun. 1976, pp. 1-7.*

"Designing Custom Peptides," from Sigma Genosys, pp. 1-2. Accessed Dec. 16, 2004.*

Schinzel R, Drueckes P, "The phosphate recognition site of *Escherichia coli* maltodextrin phosphorylase," FEBS, Jul. 1991, 286(1,2): 125-128.*

Berendsen HJC, "A Glimpse of the Holy Grail?" Science, 1998, 282: 642-643.*

Voet D, Voet JG, Biochemistry, Second Edition, John Wiley & Sons, Inc., 1995, pp. 235-241.*

Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*

Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*

Intro to cancer from Merck manual, p. 1. Accessed Mar. 5, 2008.*

Clinical aspects of cancer from Merck manual, pp. 1-4. Accessed Mar. 5, 2008.*

Auerbach R, Akhtar N, Lewis RL, Shinners BL, "Angiogenesis assays: Problems and pitfalls," cancer and Metastasis Reviews, 2000, 19: 167-172.*

Gura T, "Systems for Identifying New Drugs Are Often Faulty," Science, 1997, 278: 1041-1042.*

Jain RK, "Barriers to Drug Delivery in Solid Tumors," Scientific American, 1994, 58-65.*

* cited by examiner

*Primary Examiner* — Julie Ha
(74) *Attorney, Agent, or Firm* — Birch, Stewart, Kolasch and Birch, LLP

(57) ABSTRACT

Novel peptides useful as a therapeutic and/or prophylactic agent of cancers, as well as medical uses thereof, are described. Each of these peptides have a consecutive amino acid sequence within a specific region of YKL-40 antigen expressing on the cell surface of brain tumor cells, that is, within the region aa10-19, aa49-61, aa74-83, aa96-117, aa152-161, aa177-185, aa202-211, aa246-261 or aa326-354, which peptide has an immunity-inducing activity. These peptides are useful for therapy and/or prevention of cancers when administered to a living body, and are useful for inducing T cells which exert cytotoxic activity against cancer cells when used to stimulate the T cells in vitro.

9 Claims, 7 Drawing Sheets

SEQUENCE LISTING

<160> NUMBER OF SEQ ID NOS: 19

<210> SEQ ID NO 1
<211> LENGTH: 1149
<212> TYPE: DNA
<213> ORGANISM: Homo sapiens
<220> FEATURE:
<221> NAME/KEY: CDS
<222> LOCATION: (1)..(1149)

<400> SEQUENCE: 1

| | | | | | | | | | | | | | | | | |
|---|---|---|---|---|---|---|---|---|---|---|---|---|---|---|---|---|
| atg | ggt | gtg | aag | gcg | tct | caa | aca | ggc | ttt | gtg | gtc | ctg | gtg | ctg | ctc | 48 |
| Met | Gly | Val | Lys | Ala | Ser | Gln | Thr | Gly | Phe | Val | Val | Leu | Val | Leu | Leu | |
| 1 | | | | 5 | | | | | 10 | | | | | 15 | | |

| cag | tgc | tgc | tct | gca | tac | aaa | ctg | gtc | tgc | tac | tac | acc | agc | tgg | tcc | 96 |
|---|---|---|---|---|---|---|---|---|---|---|---|---|---|---|---|---|
| Gln | Cys | Cys | Ser | Ala | Tyr | Lys | Leu | Val | Cys | Tyr | Tyr | Thr | Ser | Trp | Ser | |
| | | | 20 | | | | | 25 | | | | | 30 | | | |

| cag | tac | cgg | gaa | ggc | gat | ggg | agc | tgc | ttc | cca | gat | gcc | ctt | gac | cgc | 144 |
|---|---|---|---|---|---|---|---|---|---|---|---|---|---|---|---|---|
| Gln | Tyr | Arg | Glu | Gly | Asp | Gly | Ser | Cys | Phe | Pro | Asp | Ala | Leu | Asp | Arg | |
| | 35 | | | | | 40 | | | | | 45 | | | | | |

| ttc | ctg | tgt | acc | cac | atc | atc | tac | agc | ttt | gcc | aat | ata | agc | aac | gat | 192 |
|---|---|---|---|---|---|---|---|---|---|---|---|---|---|---|---|---|
| Phe | Leu | Cys | Thr | His | Ile | Ile | Tyr | Ser | Phe | Ala | Asn | Ile | Ser | Asn | Asp | |
| 50 | | | | | 55 | | | | | 60 | | | | | | |

| cac | atc | gac | acc | tgg | gag | tgg | aat | gat | gtg | acg | ctc | tac | ggc | atg | ctc | 240 |
|---|---|---|---|---|---|---|---|---|---|---|---|---|---|---|---|---|
| His | Ile | Asp | Thr | Trp | Glu | Trp | Asn | Asp | Val | Thr | Leu | Tyr | Gly | Met | Leu | |
| 65 | | | | 70 | | | | | 75 | | | | | 80 | | |

| aac | aca | ctc | aac | aac | acg | aac | ccc | aac | ctg | aag | act | ctc | ttg | tct | gtc | 288 |
|---|---|---|---|---|---|---|---|---|---|---|---|---|---|---|---|---|
| Asn | Thr | Leu | Asn | Asn | Thr | Asn | Pro | Asn | Leu | Lys | Thr | Leu | Leu | Ser | Val | |
| | | | | 85 | | | | | 90 | | | | | 95 | | |

| gga | gga | tgg | aac | ttt | ggg | tct | caa | aga | ttt | tcc | aag | ata | gcc | tcc | aac | 336 |
|---|---|---|---|---|---|---|---|---|---|---|---|---|---|---|---|---|
| Gly | Gly | Trp | Asn | Phe | Gly | Ser | Gln | Arg | Phe | Ser | Lys | Ile | Ala | Ser | Asn | |
| | | | 100 | | | | | 105 | | | | | 110 | | | |

| acc | cag | agt | cgc | cgg | act | ttc | atc | aag | tca | gta | ccg | cca | ttt | ctg | cgc | 384 |
|---|---|---|---|---|---|---|---|---|---|---|---|---|---|---|---|---|
| Thr | Gln | Ser | Arg | Arg | Thr | Phe | Ile | Lys | Ser | Val | Pro | Pro | Phe | Leu | Arg | |
| | | 115 | | | | | 120 | | | | | 125 | | | | |

| acc | cat | ggc | ttt | gat | ggg | cgt | gac | ctt | gcc | tgg | ctc | tac | cct | gga | cgg | 432 |
|---|---|---|---|---|---|---|---|---|---|---|---|---|---|---|---|---|
| Thr | His | Gly | Phe | Asp | Gly | Arg | Asp | Leu | Ala | Trp | Leu | Tyr | Pro | Gly | Arg | |
| | 130 | | | | | 135 | | | | | 140 | | | | | |

| aga | gac | aaa | cac | cat | ttt | acc | acc | cta | atc | aag | gaa | atg | aag | gcc | gaa | 480 |
|---|---|---|---|---|---|---|---|---|---|---|---|---|---|---|---|---|
| Arg | Asp | Lys | His | His | Phe | Thr | Thr | Leu | Ile | Lys | Glu | Met | Lys | Ala | Glu | |
| 145 | | | | 150 | | | | | 155 | | | | | 160 | | |

| ttt | ata | aag | gaa | gcc | cag | cca | ggg | aaa | aag | cag | ctc | ctg | ctc | agc | gca | 528 |
|---|---|---|---|---|---|---|---|---|---|---|---|---|---|---|---|---|
| Phe | Ile | Lys | Glu | Ala | Gln | Pro | Gly | Lys | Lys | Gln | Leu | Leu | Leu | Ser | Ala | |
| | | | | 165 | | | | | 170 | | | | | 175 | | |

| gca | ctg | tct | gcg | ggg | aag | gtc | acc | att | gac | agc | agc | tat | gac | att | gcc | 576 |
|---|---|---|---|---|---|---|---|---|---|---|---|---|---|---|---|---|
| Ala | Leu | Ser | Ala | Gly | Lys | Val | Thr | Ile | Asp | Ser | Ser | Tyr | Asp | Ile | Ala | |
| | | | 180 | | | | | 185 | | | | | 190 | | | |

| aag | ata | tcc | caa | cac | ctg | gat | ttc | att | agc | atc | atg | acc | tac | gat | ttt | 624 |
|---|---|---|---|---|---|---|---|---|---|---|---|---|---|---|---|---|
| Lys | Ile | Ser | Gln | His | Leu | Asp | Phe | Ile | Ser | Ile | Met | Thr | Tyr | Asp | Phe | |
| | | 195 | | | | | 200 | | | | | 205 | | | | |

| cat | ggc | gcc | tgg | cgt | ggg | acc | aca | ggc | cat | cac | agt | ccc | ctc | agg | cga | 672 |
|---|---|---|---|---|---|---|---|---|---|---|---|---|---|---|---|---|
| His | Gly | Ala | Trp | Arg | Gly | Thr | Thr | Gly | His | His | Ser | Pro | Leu | Arg | Arg | |
| | 210 | | | | | 215 | | | | | 220 | | | | | |

| ggt | cag | gag | gat | gca | agt | cct | gac | aga | ttc | agc | aac | act | gac | tat | gct | 720 |
|---|---|---|---|---|---|---|---|---|---|---|---|---|---|---|---|---|
| Gly | Gln | Glu | Asp | Ala | Ser | Pro | Asp | Arg | Phe | Ser | Asn | Thr | Asp | Tyr | Ala | |
| 225 | | | | 230 | | | | | 235 | | | | | 240 | | |

| gtg | ggg | tac | atg | ttg | agg | ctg | ggg | gct | cct | gcc | agt | aag | ctg | gtg | atg | 768 |
|---|---|---|---|---|---|---|---|---|---|---|---|---|---|---|---|---|
| Val | Gly | Tyr | Met | Leu | Arg | Leu | Gly | Ala | Pro | Ala | Ser | Lys | Leu | Val | Met | |
| | | | | 245 | | | | | 250 | | | | | 255 | | |

| ggc | atc | ccc | acc | ttc | ggg | agg | agc | ttc | act | ctg | gct | tct | tct | gag | act | 816 |
|---|---|---|---|---|---|---|---|---|---|---|---|---|---|---|---|---|

-continued

```
             Gly Ile Pro Thr Phe Gly Arg Ser Phe Thr Leu Ala Ser Ser Glu Thr
                         260                 265                 270 ggt gtt cca gcg cca atc tca gga ccg gga att cca ggc cgg ttc acc       864
Gly Val Pro Ala Pro Ile Ser Gly Pro Gly Ile Pro Gly Arg Phe Thr
            275                 280                 285 aag gag gca ggg acc ctt gcc tac tat gag atc tgt gac ttc ctc cgc       912
Lys Glu Ala Gly Thr Leu Ala Tyr Tyr Glu Ile Cys Asp Phe Leu Arg
        290                 295                 300 gga gcc aca gtc cat aga acc ctc ggc cag cag gtc ccc tat gcc acc       960
Gly Ala Thr Val His Arg Thr Leu Gly Gln Gln Val Pro Tyr Ala Thr
305                 310                 315                 320 aag ggc aac cag tgg gta gga tac gac gac cag gaa agc gtc aaa agc      1008
Lys Gly Asn Gln Trp Val Gly Tyr Asp Asp Gln Glu Ser Val Lys Ser
                325                 330                 335 aag gtg cag tac ctg aag gat agg cag ctg gca ggc gcc atg gta tgg      1056
Lys Val Gln Tyr Leu Lys Asp Arg Gln Leu Ala Gly Ala Met Val Trp
            340                 345                 350 gcc ctg gac ctg gat gac ttc cag ggc tcc ttc tgc ggc cag gat ctg      1104
Ala Leu Asp Leu Asp Asp Phe Gln Gly Ser Phe Cys Gly Gln Asp Leu
        355                 360                 365 cgc ttc cct ctc acc aat gcc atc aag gat gca ctc gct gca acg          1149
Arg Phe Pro Leu Thr Asn Ala Ile Lys Asp Ala Leu Ala Ala Thr
370                 375                 380

<210> SEQ ID NO 2
<211> LENGTH: 383
<212> TYPE: PRT
<213> ORGANISM: Homo sapiens

<400> SEQUENCE: 2

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
            20                  25                  30

Gln Tyr Arg Glu Gly Asp Gly Ser Cys Phe Pro Asp Ala Leu Asp Arg
        35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Asn Asn Thr Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Arg Asp Leu Ala Trp Leu Tyr Pro Gly Arg
    130                 135                 140

Arg Asp Lys His His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Arg Arg
    210                 215                 220
```

```
Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
            245                 250                 255

Gly Ile Pro Thr Phe Gly Arg Ser Phe Thr Leu Ala Ser Ser Glu Thr
        260                 265                 270

Gly Val Pro Ala Pro Ile Ser Gly Pro Gly Ile Pro Gly Arg Phe Thr
    275                 280                 285

Lys Glu Ala Gly Thr Leu Ala Tyr Tyr Glu Ile Cys Asp Phe Leu Arg
290                 295                 300

Gly Ala Thr Val His Arg Thr Leu Gly Gln Gln Val Pro Tyr Ala Thr
305                 310                 315                 320

Lys Gly Asn Gln Trp Val Gly Tyr Asp Asp Gln Glu Ser Val Lys Ser
            325                 330                 335

Lys Val Gln Tyr Leu Lys Asp Arg Gln Leu Ala Gly Ala Met Val Trp
        340                 345                 350

Ala Leu Asp Leu Asp Asp Phe Gln Gly Ser Phe Cys Gly Gln Asp Leu
    355                 360                 365

Arg Phe Pro Leu Thr Asn Ala Ile Lys Asp Ala Leu Ala Thr
370                 375                 380

<210> SEQ ID NO 3
<211> LENGTH: 17
<212> TYPE: PRT
<213> ORGANISM: Homo sapiens

<400> SEQUENCE: 3

Phe Gly Ser Gln Arg Phe Ser Lys Ile Ala Ser Asn Thr Gln Ser Arg
1               5                   10                  15

Arg

<210> SEQ ID NO 4
<211> LENGTH: 10
<212> TYPE: PRT
<213> ORGANISM: Homo sapiens

<400> SEQUENCE: 4

Ser Ile Met Thr Tyr Asp Phe His Gly Ala
1               5                   10

<210> SEQ ID NO 5
<211> LENGTH: 9
<212> TYPE: PRT
<213> ORGANISM: Homo sapiens

<400> SEQUENCE: 5

Gln Leu Ala Gly Ala Met Val Trp Ala
1               5

<210> SEQ ID NO 6
<211> LENGTH: 9
<212> TYPE: PRT
<213> ORGANISM: Homo sapiens

<400> SEQUENCE: 6

Ala Leu Ser Ala Gly Lys Val Thr Ile
1               5

<210> SEQ ID NO 7
<211> LENGTH: 9
```

```
<212> TYPE: PRT
<213> ORGANISM: Homo sapiens

<400> SEQUENCE: 7

Val Gly Tyr Asp Asp Gln Glu Ser Val
1               5

<210> SEQ ID NO 8
<211> LENGTH: 9
<212> TYPE: PRT
<213> ORGANISM: Homo sapiens

<400> SEQUENCE: 8

Phe Leu Cys Thr His Ile Ile Tyr Ser
1               5

<210> SEQ ID NO 9
<211> LENGTH: 9
<212> TYPE: PRT
<213> ORGANISM: Homo sapiens

<400> SEQUENCE: 9

Ser Val Lys Ser Lys Val Gln Tyr Leu
1               5

<210> SEQ ID NO 10
<211> LENGTH: 9
<212> TYPE: PRT
<213> ORGANISM: Homo sapiens

<400> SEQUENCE: 10

His Ile Ile Tyr Ser Phe Ala Asn Ile
1               5

<210> SEQ ID NO 11
<211> LENGTH: 9
<212> TYPE: PRT
<213> ORGANISM: Homo sapiens

<400> SEQUENCE: 11

Lys Leu Val Met Gly Ile Pro Thr Phe
1               5

<210> SEQ ID NO 12
<211> LENGTH: 10
<212> TYPE: PRT
<213> ORGANISM: Homo sapiens

<400> SEQUENCE: 12

Gln Leu Ala Gly Ala Met Val Trp Ala Leu
1               5                   10

<210> SEQ ID NO 13
<211> LENGTH: 10
<212> TYPE: PRT
<213> ORGANISM: Homo sapiens

<400> SEQUENCE: 13

Arg Leu Gly Ala Pro Ala Ser Lys Leu Val
1               5                   10

<210> SEQ ID NO 14
<211> LENGTH: 10
<212> TYPE: PRT
<213> ORGANISM: Homo sapiens
```

```
<400> SEQUENCE: 14

Thr Leu Ile Lys Glu Met Lys Ala Glu Phe
1               5                   10

<210> SEQ ID NO 15
<211> LENGTH: 10
<212> TYPE: PRT
<213> ORGANISM: Homo sapiens

<400> SEQUENCE: 15

Phe Leu Cys Thr His Ile Ile Tyr Ser Phe
1               5                   10

<210> SEQ ID NO 16
<211> LENGTH: 10
<212> TYPE: PRT
<213> ORGANISM: Homo sapiens

<400> SEQUENCE: 16

Phe Val Val Leu Val Leu Leu Gln Cys Cys
1               5                   10

<210> SEQ ID NO 17
<211> LENGTH: 10
<212> TYPE: PRT
<213> ORGANISM: Homo sapiens

<400> SEQUENCE: 17

Val Thr Leu Tyr Gly Met Leu Asn Thr Leu
1               5                   10

<210> SEQ ID NO 18
<211> LENGTH: 22
<212> TYPE: PRT
<213> ORGANISM: Homo sapiens

<400> SEQUENCE: 18

Val Gly Gly Trp Asn Phe Gly Ser Gln Arg Phe Ser Lys Ile Ala Ser
1               5                   10                  15

Asn Thr Gln Ser Arg Arg
            20

<210> SEQ ID NO 19
<211> LENGTH: 9
<212> TYPE: PRT
<213> ORGANISM: Homo sapiens

<400> SEQUENCE: 19

Leu Gln Cys Cys Ser Ala Tyr Lys Leu
1               5
```

CANCER ANTIGEN PEPTIDE AND THE USE THEREOF

TECHNICAL FIELD

The present invention relates to proteins specific to human cancers, partial peptides thereof and their uses. The present invention further relates to polynucleotides coding for the peptides, activated T cells stimulated and induced by the peptides, antigen presenting cells containing complexes between the peptides and HLA molecules, antibodies to the peptides, and to pharmaceuticals containing the peptides and/or antibodies.

BACKGROUND ART

Cancers are the commonest cause for death among all of the causes for death. The therapies therefor are mainly surgical treatment in combination with radiotherapy and chemotherapy. In spite of the developments of new surgical methods and discovery of new anti-cancer agents in recent years, treatment results of cancers are not improved very much at present except for some cancers.

In recent years, by virtue of the development in molecular biology and cancer immunology, cancer antigens recognized by cytotoxic T cells reactive with cancers, as well as the genes encoding the cancer antigens, were identified, and expectations for antigen-specific immunotherapies have been raised (see Non-patent Literature 1). In 1991 Boon et al of Ludwig Institute in Belgium isolated human melanoma antigen MAGE 1 recognized by CD8-positive T cells by a cDNA-expression cloning method using an autologous cancer cell line and cancer-reactive T cells (see Non-patent Literature 2). After the report by Boon, antigens recognized by CD8-positive T cells, such as tyrosinase (see Non-patent Literature 3), MART1/MelanA (see Non-patent Literature 4) and gp100 (see Non-patent Literature 5) have been isolated.

In immunotherapy, to reduce side effects, it is desired that the protein recognized as the antigen be one which exists in a small amount in normal cells and exists in an excess amount in cancer cells. Further, it is desired that the antigen protein contain, in addition to the peptide region which can induce antigen-specific cytotoxic T cells which directly attack the tumor expressing the antigen, a peptide region which can induce antigen-specific helper T cells that aid the activity of the cytotoxic T cells.

Recently, the possibility that YKL-40 may be used as a tumor marker in serum associated with human malignant brain tumor was suggested. It has been reported that this protein is excessively expressed in most of human malignant brain tumors and is not substantially expressed in normal brain tissues (see Non-patent Literature 6).

Non-patent Literature 1: Tsuyoshi AKIYOSHI, "Japanese Journal of Cancer and Chemotherapy", 1997, vol. 24, p 551-519

Non-patent Literature 2: Bruggen P. et al., Science, 254: 1643-1647 (1991)

Non-patent Literature 3: Robbins P. F. et al., Cancer Res., 54: 3124-3126 (1994)

Non-patent Literature 4: Kawakami Y. et al., Proc. Natl. Acad. Sci. USA, 91(9): 3515-3519 (1994)

Non-patent Literature 5: Kawakami Y. et al., Proc. Natl. Acad. Sci. USA, 91: 6458-6462 (1994)

Non-patent Literature 6: Meena K. et al., Cancer Res., 62: 4364-4368 (2002)

DISCLOSURE OF THE INVENTION

Problems which the Invention Tries to Solve

An object of the present invention is to provide a novel peptide useful as a therapeutic and/or prophylactic agent for a cancer(s). Another object of the present invention is to provide a use of the peptide as a therapeutic and/or prophylactic agent for a cancer(s) and as an agent for treating antigen presenting cells. Still another object of the present invention is to provide an isolated antigen presenting cell containing a complex between the peptide and an HLA molecule, and an isolated T cell which selectively binds the complex between the peptide and HLA molecule, as well as their uses as a therapeutic and/or prophylactic agent for a cancer(s).

Means for Solving the Problems

The present inventors discovered that the partial peptides existing in specific regions in the above-described YKL-40 having the amino acid sequence shown in. SEQ ID NO:2 are presented by antigen presenting cells, and have the ability (immunity-inducing activity) of activating and proliferating cytotoxic T cells specific thereto, so that the peptides are useful for the therapy and/or prevention of cancers, and the antigen presenting cells contacted with the peptide and the T cells contacted with the antigen presenting cells are useful for the therapy and/or prevention of cancers, thereby completing the present invention.

That is, the present invention provides a peptide having not less than 7 consecutive amino acids in the region of aa10-19, aa49-61, aa74-83, aa96-117, aa152-161, aa177-185, aa202-211, aa246-261 or aa326-354 in SEQ ID NO:2 in SEQUENCE LISTING, which peptide has an immunity-inducing activity, or a peptide having 7 to 30 amino acid residues having an identity of not less than 80% to any one of the peptides, which peptide has an immunity-inducing activity, or a peptide having 8 to 31 amino acid residues, comprising any one of the above-described peptides as a partial sequence thereof, which peptide has an immunity-inducing activity. The present invention also provides a polynucleotide cording for the above-described peptide of the present invention. The present invention further provides a pharmaceutical comprising as an effective ingredient the above-described peptide of the present invention. The present invention still further provides a therapeutic and/or prophylactic agent of a cancer(s), comprising as an effective ingredient the above-described peptide of the present invention. The present invention still further provides a use of the above-described peptide of the present invention for the production of a therapeutic and/or prophylactic agent of a cancer(s). The present invention still further provides a method for treating and/or preventing a cancer(s), comprising administering an effective amount of the above-described peptide of the present invention an individual. The present invention still further provides an agent for treating antigen presenting cells, the agent comprising the above-described peptide of the present invention. The present invention still further provides a use of the above-described peptide of the present invention for the production of an agent for treating antigen presenting cells. The present invention still further provides a method for treating antigen presenting cells, the method comprising bringing the antigen presenting cells into contact with the above-described peptide of the present invention. The present invention still further provides an isolated antigen presenting cell comprising a complex between the above-described peptide of the present invention and an HLA molecule. The present invention still further provides a method for activating T cells, comprising bringing the above-described isolated antigen presenting cell of the present invention into contact with a T cell(s). The present invention still further provides an isolated T cell which selectively binds a complex between the above-described peptide of the present invention and an HLA molecule. The present invention still further provides a pharmaceutical comprising as an effective ingredient the above-described isolated antigen presenting cell of the present invention and/or the above-described isolated T cell of the present invention. The present invention still further provides a therapeutic and/or prophylactic agent of a cancer(s), comprising as an effective ingredient the above-described isolated antigen presenting cell of the present invention and/or the above-described isolated T cell of the present invention. The present invention still further provides a method for treating and/or preventing a cancer(s), comprising administering an effective amount of the above-described isolated antigen presenting cell of the present invention and/or the above-described isolated T cell of the present invention. The present invention still further provides an antibody whose corresponding antigen is the above-described peptide of the present invention, or an antigen-binding fragment thereof. The present invention still further provides a diagnostic agent of a cancer(s), the diagnostic agent comprising the above-described antibody or the antigen-binding fragment thereof according to the present invention. The present invention still further provides a cancer-specific immunity-inducing agent comprising as an effective ingredient a protein having the amino acid sequence shown in SEQ ID NO:2 or a protein having an immunity-inducing activity, which protein has an amino acid sequence with an identity of not less than 80% to the amino acid sequence shown in SEQ ID NO:2.

Effects of the Invention

By the present invention, novel peptides useful for the therapies and/or prophylactics of cancers, and for induction of antigen presenting cells and T cells therefor, as well as various uses of the peptides in medical field were provided. As will be concretely described in the examples below, the CD8-positive T cells activated by the peptide of the present invention exhibits excellent cytotoxic activity against cancer cells expressing YKL-40. Therefore, the peptides of the present invention are useful for therapies and/or prophylactics of cancers, by being administered to human, or by administering T cells to human, which T cells were activated by the peptides.

BRIEF DESCRIPTION OF THE INVENTION

BEST MODE FOR CARRYING OUT THE INVENTION

Figure 1:
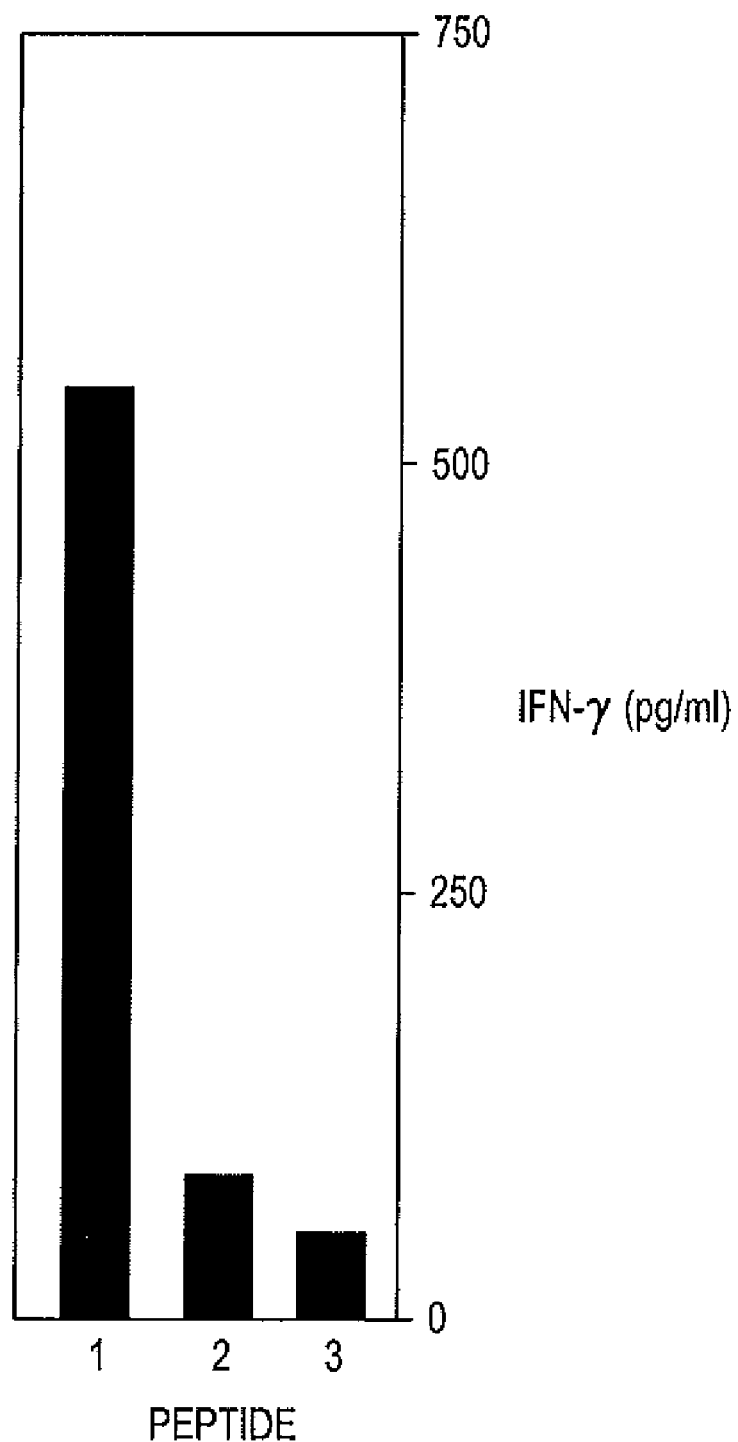
FIG. 1 shows that peptide-specific CD8-positive % T cells recognize the complex between the peptide and HLA-A0201 and produce IFN-γ.

As described above, as the peptides of the present invention, the peptides each of which has not less than 7 consecutive amino acids in the region of aa10-19, aa49-61, aa74-83, aa96-117, aa152-161, aa177-185, aa202-211, aa246-261 or aa326-354 in SEQ ID NO:2 in SEQUENCE LISTING, which peptide has an immunity-inducing activity (hereinafter referred to as "immunity-inducing partial peptide" for convenience) are first enumerated.

The symbol "aa" herein means the number of the amino acid residue counted from the N-terminal of the amino acid sequence. For example, "aa10" means that the amino acid residue is the 10th amino acid residue counted from the N-terminal, and "region of aa10-19" means the region consisting of 10 amino acid residues from the 10th amino acid residue counted from the N-terminal to the 19th amino acid residue. The term "immunity-inducing activity" means the ability to activate and proliferate the T cells reactive with cancer cells expressing YKL-40. More concretely, the term means that the IFN-γ-producing ability and/or cytotoxic activity against YKL-40-expressing cancer cells of the T cells stimulated with a peptide, which is(are) measured by the methods described in detail in the examples below, is(are) higher than that(those) of the control T cell not stimulated with the peptide, and the T cell stimulated with the peptide proliferates better than the control T cell not stimulated with the peptide. The proliferation may be confirmed by visual observation, counting the number of cells under microscope, flow cytometry, intake of tritium-labelled thymidine into the cells, or the like. The measurement of the IFN-γ-producing ability, employed in the examples below is described in, for example, J. Immunol., 154, p 2257, 1995, and the measurement of the cytotoxic activity is based on a known method called $^{51}Cr$ release assay described in Int. J. Cancer, 58: p 317, 1994.

Preferred examples of the peptides of the present invention include the peptides having the amino acid sequences shown in SEQ ID NO:3 to SEQ ID NO:19, respectively. The SEQ ID NO, amino acid sequence and position thereof in SEQ ID NO:2 of each of the peptides are shown in Table 1 below. In the present invention, the term "having the amino acid sequence" means that amino acid residues are aligned in that order. Thus, for example, the term "peptide having the amino acid sequence shown in SEQ ID NO:3" means the peptide having a size of 17 amino acids, whose amino acid sequence is Phe Gly Ser Gln Arg Phe Ser Lys Ile Ala Ser Asn Thr Gln Ser Arg Arg (SEQ ID NO:3). Further, "peptide having the amino acid sequence shown in SEQ ID NO:3" may also be referred to as "peptide of SEQ ID NO:3" for short.

TABLE 1

| SEQ ID NO: | Sequence | Position (aa) |
|---|---|---|
| 3 | Phe Gly Ser Gln Arg Phe Ser Lys Ile Ala Ser Asn Thr Gln Ser Arg Arg | 101-117 |
| 4 | Ser Ile Met Thr Tyr Asp Phe His Gly Ala | 202-211 |
| 5 | Gln Leu Ala Gly Ala Met Val Trp Ala | 345-353 |

TABLE 1-continued

| SEQ ID NO: | Sequence | | | | | | | | | | Position (aa) |
|---|---|---|---|---|---|---|---|---|---|---|---|
| 6 | Ala | Leu | Ser | Ala | Gly | Lys | Val | Thr | Ile | | 177-185 |
| 7 | Val | Gly | Tyr | Asp | Asp | Gln | Glu | Ser | Val | | 326-334 |
| 8 | Phe | Leu | Cys | Thr | His | Ile | Ile | Tyr | Ser | | 49-57 |
| 9 | Ser | Val | Lys | Ser | Lys | Val | Gln | Tyr | Leu | | 333-341 |
| 10 | His | Ile | Ile | Tyr | Ser | Phe | Ala | Asn | Ile | | 53-61 |
| 11 | Lys | Leu | Val | Met | Gly | Ile | Pro | Thr | Phe | | 253-261 |
| 12 | Gln | Leu | Ala | Gly | Ala | Met | Val | Trp | Ala | Leu | 345-354 |
| 13 | Arg | Leu | Gly | Ala | Pro | Ala | Ser | Lys | Leu | Val | 246-255 |
| 14 | Thr | Leu | Ile | Lys | Glu | Met | Lys | Ala | Glu | Phe | 152-161 |
| 15 | Phe | Leu | Cys | Thr | His | Ile | Ile | Tyr | Ser | Phe | 49-58 |
| 16 | Phe | Val | Val | Leu | Val | Leu | Leu | Gln | Cys | Cys | 10-19 |
| 17 | Val | Thr | Leu | Tyr | Gly | Met | Leu | Asn | Thr | Leu | 74-83 |
| 18 | Val Phe Arg | Gly Ser Arg | Gly Lys | Trp Ile | Asn Ala | Phe Ser | Gly Asn | Ser Thr | Gln Gln | Arg Ser | 96-117 |

The peptides each of which has the same amino acid sequence as that of the above-described peptide of the present invention except that one to several amino acid residues are substituted, deleted and/or inserted, which sequence has an identity of not less than 80%, preferably not less than 90% to the sequence of the original peptide, and which peptide has an immunity-inducing activity and has 7 to 30 amino acid residues (hereinafter referred to as "immunity-inducing modified peptide" for convenience), may also be used for therapies and/or prophylaxes of cancers or the like and are within the scope of the present invention. The term "identity" of amino acid sequences herein means the value calculated by aligning the two polypeptides such that the number of matched amino acid residues is the maximum (a gap(s) is(are) inserted as required), and dividing the number of mismatched amino acid residues by the number of amino acid residues of the full length sequence (in cases where the numbers of total amino acid residues are different between the two sequences, the number of the amino acid residues of the shorter sequence). Such a calculation of the identity may be easily attained by a well-known software such as BLAST. The 20 types of amino acids constituting the naturally occurring proteins may be classified into groups each of which has similar properties, that is, into neutral amino acids with side chains having low polarity (Gly, Ile, Val, Leu, Ala, Met, Pro), neutral amino acids having hydrophilic side chains (Asn, Gln, Thr, Ser, Tyr, Cys), acidic amino acids (Asp, Glu), basic amino acids (Arg, Lys, His) and aromatic amino acids (Phe, Tyr, Trp). It is known that, in most cases, substitutions of amino acids within the same group do not change the properties of the peptides. Therefore, in cases where the amino acid residue(s) of the above-described immunity-inducing partial peptides of the present invention is(are) substituted, the probability that the immunity-inducing activity is retained may be made high by conducting the substitution(s) within the same group.

The peptides containing the above-described peptide of the present invention (the immunity-inducing partial peptide or immunity-inducing modified peptide) as a partial sequence (i.e., the peptides of the present invention to which other peptide(s) is(are) attached to one terminal or both terminals thereof), which has 8 to 31 amino acid residues and has immunity-inducing activity (hereinafter also referred to as "immunity-inducing added peptide" for convenience) may also be used for therapies and/or prophylaxes of cancers or the like and are within the scope of the present invention.

The above-described peptides of the present invention may easily be synthesized by a conventional method using a commercially available peptide synthesizer.

The present invention provides polynucleotides coding for the above-described peptides of the present invention. The polynucleotide may be either DNA or RNA. The base sequence of the gene coding for YKL-40 is known as shown in SEQ ID NO:1. Therefore, the polynucleotide coding for the immunity-inducing partial peptide of the present invention may be one, among the base sequence shown in SEQ ID NO:1, having the base sequence of the region coding for the immunity-inducing partial peptide. Alternatively, a base sequence having a conservative substituted sequence (the amino acid sequence encoded thereby is the same but has a different base sequence) may be used. Since the codons coding for each amino acid are known, the base sequence of a polynucleotide coding for a particular amino acid sequence may easily be specified. Therefore, the base sequences of the polynucleotides coding for the immunity-inducing modified peptides and immunity-inducing added peptides may easily be specified. These polynucleotides may be synthesized by a conventional method using a commercially available nucleic acid synthesizer.

The present invention also provides recombinant vectors which contain the polynucleotide of the present invention and which can express the polynucleotide in a cell. The cell may be a mammalian cell, or a cell of a prokaryote such as E. coli or yeast, or of a eukaryotic microorganism. The vector for transferring a gene into a mammalian cell may be either a plasmid vector or virus vector. These vectors per se are well-known, and since various vectors are commercially available, these commercially available vectors may be used. By inserting the above-described polynucleotide of the present invention into a multicloning site of a commercially available vector, the recombinant vector of the present invention may be obtained.

The recombinant vectors having the polynucleotide of the present invention incorporated into a vector for gene transfer into a mammalian cell may be used as gene vaccines for therapies and/or prophylaxes of cancers. The administration route of the gene vaccine is preferably a parenteral route such as intramuscular, subcutaneous, intravenous or intraarterial administration. The dose may be appropriately selected depending on the type of the antigen or the like, and usually about 0.1 µg to 100 mg, preferably about 1 µg to 10 mg in terms of the weight of the gene vaccine per 1 kg of body weight.

Methods using a virus vector include those wherein the DNA of the present invention is incorporated into an RNA virus or DNA virus such as retrovirus, adenovirus, adeno-associated virus, herpes virus, vaccinia virus, pox virus, poliovirus or Sindbis virus, and the resulting virus is introduced. Among these methods, those using retrovirus, adenovirus, adeno-associated virus, vaccinia virus or the like are preferred.

Other methods include the method wherein an expression plasmid is directly intramuscularly administered (DNA vaccine method), liposome method, lipofectin method, microinjection method, calcium phosphate method, electroporation method and the like, and DNA vaccine method and liposome method are especially preferred.

Methods for actually making the gene coding for the peptide of the present invention act as a pharmaceutical include in vivo method wherein the gene is directly introduced into the body, and ex vivo method wherein a kind of cells are collected from human, the gene is introduced into the cells ex vivo, and the cells are returned to the body (Nikkei Science, 1994, April, p 20-45; The Pharmaceutical Monthly, 1994, Vol. 36, No. 1, p. 23-48, Experimental Medicine, Extra Edition, 1994, Vol. 12, No. 15; and references cited in these papers and the like). In vivo method is more preferred.

In cases where the gene is administered by the in vivo method, the gene may be administered through an appropriate administration route depending on the disease to be treated, symptom and so on. It may be administered, for example, by intravenous, intraarterial, subcutaneous, intramuscular administration or the like. In cases where the DNA is administered by the in vivo method, the DNA may be formulated to a preparation such as solution, and usually formulated into an injection solution or the like containing the DNA of the present invention as an effective ingredient. A commonly used carrier(s) may be added as required. In case of a liposome or membrane fusion liposome (Sendai virus (HVJ)-liposome or the like) containing the DNA of the present invention, the liposome may be formulated into a liposome preparation such as suspension, frozen preparation or centrifugally concentrated frozen preparation.

On the other hand, vectors for microorganisms such as E. coli and yeasts are well-known, and various such vectors are commercially available. The recombinant vectors obtained by incorporating the polynucleotide of the present invention into a vector for microorganisms may be used for producing the peptide of the present invention by a genetic engineering method in a large scale. Introduction of the recombinant vector into a microorganism may be carried out by a well-known method.

As will be concretely described in the examples below, the peptides of the present invention exhibit immunity-inducing activity. More particularly, the T cells stimulated with the peptide of the present invention exhibit cytotoxic activity to cancer cells expressing YKL-40, and proliferate. Therefore, by administering the peptide of the present invention to a living body, therapy and/or prophylaxis of a cancer(s) may be attained. Thus, the present invention provides a therapeutic and/or prophylactic agent for cancer(s), comprising as an effective ingredient the peptide of the present invention.

The cancers to be targeted by the therapeutic and/or prophylactic agent of the present invention are the cancers expressing YKL-40, and examples thereof include brain tumor; squamous cell carcinoma of head, neck, lung, uterus and esophagus; melanoma; adenocarcinoma of lung and uterus; and stomach cancer. The subjects to be treated are mammals, and human is particularly preferred.

Although the therapeutic and/or prophylactic agent containing as an effective ingredient the peptide of the present invention may be administered either orally or parenterally, parenteral administrations such as intramuscular, subcutaneous, intravenous and intraarterial administration are preferred. The dose may be any dose as long as the dose is effective for the therapy and/or prophylaxis of a cancer(s), and may be appropriately selected depending on the symptom, purpose of use and so on. Usually, the dose is 0.0001 mg to 1000 mg, preferably 0.001 mg to 1000 mg, and this dose is preferably administered once per several days to once per several months.

The therapeutic and/or prophylactic agent containing as an effective ingredient the peptide of the present invention may be formulated using a pharmaceutically acceptable carrier(s) and/or diluent(s) suitable for each administration mode. Formulation methods and various carriers therefor are well-known in the field of formulation of pharmaceuticals. Examples of the pharmaceutically acceptable carriers or diluents include buffer solutions such as physiological buffer solutions; and vehicles (such as sucrose, lactose, corn starch, calcium phosphate, sorbitol and glycine), and a binder(s) (such as syrup, gelatin, gum arabic, sorbitol, polyvinyl chloride and tragacanth) and/or a lubricant(s) (such as magnesium stearate, polyethylene glycol, talc and silica) may also be admixed optionally. Administration modes include oral preparations such as tablets, capsules, granules, powders and syrups; and parenteral preparations such as inhalants, injection solutions, suppositories and solutions. These preparations may be formulated by generally known methods.

The therapeutic and/or prophylactic agent containing as an effective ingredient the peptide of the present invention may be in the form of a vaccine. In this case, the vaccine preferably contains an adjuvant in addition to the effective ingredient. Adjuvants provide a reservoir of the antigen (outside cells or in macrophages), activate macrophages, and increase immunological response by stimulating a specific class of lymphocytes. A number of types of adjuvants are well-know in the art. Specific examples of the adjuvants include MPL (SmithKline Beecham) and homologues of *Salmonella minnesota* Re 595 lipopolysaccharide obtained after purification and acid hydrolysis of the lipopolysaccharide; QS21 (SmithKline Beecham), pure QA-21 saponin purified from extraction of *Quillja saponaria*; DQS21 described in WO96/33739 (SmithKline Beecham); QS-7, QS-17, QS-18 and QS-L1 (So and 10 others, "Molecules and cells", 1997, Vol. 7, p. 178-186); Freund's incomplete adjuvant; Freund's complete adjuvant; vitamin E; Montanide; alum; CpG oligonucleotides (see, for example, Kreig and 7 others, "Nature", Vol. 374, p. 546-549); and various water in oil emulsions prepared from biodegradable oils such as squalene and/or tocopherol. Preferably, the peptide is administered after being mixed with the combination of DQS21/MPL. The ratio of DSQ21 to MPL is typically about 1:10 to 10:1, preferably about 1:5 to 5:1, more preferably about 1:1. Typically, for administration to humans, DQS21 and MPL exist in a vaccine preparation in an amount of about 1 µg to about 100 µg. Other adjuvants are known in the art and may be used in the present invention (e.g., see Goding, "Monoclonal Antibodies: Principles and Practice", 2nd edition, 1986). Methods for preparation of mixtures of a peptide and adjuvant are well-known for those skilled in the art of vaccination.

Other factors which stimulate the immune response of the subject may also be administered. For example, other cytokines are useful for the vaccination protocol as a result of lymphocyte-stimulating properties. Examples thereof include interleukin-12 (IL-12), GM-CSF, IL-18 and Flt3 ligand, which have been shown to promote the prophylactic action of vaccines. When the therapeutic composition of the present invention is administered, the composition is administered in the form of pharmaceutically acceptable formulation. Such a formulation may routinely contain a salt at a pharmaceutically acceptable concentration, buffering agent, antiseptic, miscible carrier, immunoadjuvant. e.g., an adjuvant and cytokine, and optionally other therapeutic agonists.

As will be concretely shown in the examples below, by bringing the peptide of the present invention into contact with antigen presenting cells in vitro, the antigen presenting cells may be made to present the peptide of the present invention.

Thus, the present invention also provides an agent for treating antigen presenting cells, comprising the above-described peptide of the present invention. Here, as the antigen presenting cells, dendritic cells and/or B cells, which have HLA class I or HLA class II molecules may preferably be employed. Various HLA class I and HLA class II molecules have been identified and well-known. Examples of HLA class I molecules include HLA-A, HLA-B and HLA-C, more specifically, HLA-A1, HLA-A0201, HLA-A0204, HLA-A0205, HLA-A0206, HLA-A0207, HLA-A11, HLA-A24, HLA-A31, HLA-A6801, HLA-B7, HLA-B8, HLA-B2705, HLA-B37, HLA-Cw0401, HLA-Cw0602 and the like. Examples of HLA class II molecules include HLA-DR, HLA-DQ and HLA-DP.

The dendritic cells or B cells having HLA class I or HLA class II molecules may be prepared from peripheral blood by a well-known method. For example, tumor-specific dendritic cells may be induced by inducing dendritic cells from bone marrow, umbilical cord blood or patient's peripheral blood using granulocyte-macrophage colony-stimulating factor (GM-CSF) and IL-3 (or IL-4), and adding a tumor-related peptide to the culture system. By administering an effective amount of such dendritic cells, a response desired for the therapy of cancers may be induced. As the cells to be used, bone marrow or umbilical cord blood donated from a healthy individual, or bone marrow, peripheral blood or the like from the patient himself may be used. Using autologous cells of the patient is highly safe and serious side effects are expected to be avoided. The peripheral blood or bone marrow may be either fresh sample, cold-stored sample or frozen sample. As for peripheral blood, whole blood may be cultured or leukocyte component alone may be separated and cultured, and the latter is effective and preferred. Further, among the leukocyte component, mononuclear cells may be separated. In cases where the cells are originated from bone marrow or umbilical cord blood, the whole cells constituting the bone marrow may be cultured, or mononuclear cells may be separated and cultured. In peripheral blood or leukocyte component thereof, or in bone marrow cells, mononuclear cells, hematopoietic stem cells, or immature dendritic cells or CD4-positive cells and the like are contained. As for the cytokine to be used, the production method thereof is not restricted and naturally-occurring or recombinant cytokine or the like may be employed as long as its safety and physiological activity have been confirmed. Preferably, a preparation confirmed to have medical quality is used in a minimum necessary amount. The concentration of the cytokine(s) to be added is not restricted as long as the dendritic cells are induced, and usually, the total concentration of the cytokine(s) is preferably about 10 to 1000 ng/mL, more preferably about 20 to 500 ng/mL. The culture may be carried out using a well-known medium usually used for the culture of leukocytes. The culturing temperature is not restricted as long as the proliferation of the leukocytes is attained, and about 37° C. which is the body temperature of human is most preferred. The atmospheric environment during the culturing is not restricted as long as the proliferation of leukocytes is attained, and to flow 5% $CO_2$ is preferred. The culturing period is not restricted as long as the necessary number of the cells is induced, and is usually 3 days to 8 weeks. As for the apparatuses used for separation and culturing of the cells, appropriate apparatuses, preferably those whose safety when applied to medical uses have been confirmed, and whose operations are stable and simple, may be employed. Particularly, as for the cell-culturing apparatus, not only the general vessels such as Petri dish, flask and bottle, but also a layer type vessel, multistage vessel, roller bottle, spinner type bottle, bag type culturing vessel, hollow fiber column and the like may be used.

Bringing the peptide of the present invention into contact with the antigen presenting cells in vitro may be carried out by a well-known method, and is concretely described in the examples below. That is, it may be carried out by culturing the cells in a culture medium containing the peptide of the present invention. The concentration of the peptide in the medium is not restricted, and usually about 1 μg/ml to 100 μg/ml, preferably about 5 μg/ml to 20 μg/ml. The cell density during the culturing is not restricted and is usually about $10^3$ cells/ml to $10^7$ cells/ml, preferably $5 \times 10^4$ cells/ml to $5 \times 10^6$ cells/ml. The culturing may be carried-out according to a conventional method, and is preferably carried out at 37° C. under atmosphere of 5% $CO_2$.

By culturing the antigen presenting cells in the presence of the above-described peptide, the peptide is incorporated into HLA molecules of the antigen presenting cells, and is presented on the surfaces of the antigen presenting cells. The present invention also provides an isolated antigen presenting cell comprising the complex between the peptide of the present invention and the HLA molecule. Such an antigen presenting cell presents the peptide to T cells in vivo or in vitro, and induces and proliferates cytotoxic T cells specific to the peptide.

By bringing the antigen presenting cells comprising the complex between the peptide of the present invention and HLA molecule into contact with T cells, cytotoxic T cells specific to the peptide may be induced and proliferated. This may be carried out by co-culturing the above-described antigen presenting cells and T cells in a liquid medium. For example, it may be attained by suspending the antigen presenting cells in a liquid medium, placing the suspension in vessels such as wells of a microplate, adding thereto T cells and culturing the cells. The mixing ratio of the antigen presenting cells to the T cells in the co-culturing is not restricted, and is usually about 1:1 to 1:100, preferably about 1:5 to 1:20 in terms of the number of cells. The density of the antigen presenting cells suspended in the liquid medium is not restricted, and is usually about 100 to 10,000,000 cells/ml, preferably about 10,000 to 1,000,000 cells/ml. The co-culturing is preferably carried out at 37° C. under atmosphere of 5% $CO_2$ in accordance with the conventional method. The culturing time is not restricted, and is usually 2 days to 3 weeks, preferably about 4 days to 2 weeks. The co-culturing is preferably carried out in the presence of one or more interleukins such as IL-2, IL-6, IL-7 and IL-12. In this case, the concentration of IL-2 and IL-7 is usually about 5 U/ml to 20 U/ml, the concentration of IL-6 is usually about 500 U/ml to 2000 U/ml, and the concentration of IL-12 is usually about 5 ng/ml to 20 ng/ml, but the concentrations of the interleukins are not restricted thereto. The above-described co-culturing may be repeated once to several times adding fresh antigen presenting cells. For example, an operation of discarding the culture supernatant after the co-culturing and adding a suspension of fresh antigen presenting cells to further conducting the co-culturing may be repeated once to several times. The conditions of the each co-culturing may be the same as described above. In the present specification, the operation of adding the peptide of the present invention to the culture medium of the antigen presenting cells in order to make the antigen presenting cells present the peptide on their surfaces may be called "pulse the cells with the peptide". The operation of bringing the antigen presenting cells presenting the peptide of the present invention into contact with the T cells may be called "stimulate the T cells with the peptide".

By the above-described co-culturing, cytotoxic T cells specific to the peptide are induced and proliferated. The present invention also provides such an isolated T cell which selectively binds the complex between the peptide of the present invention and HLA molecule.

Since the above-described antigen presenting cells which present the peptide of the present invention can induce and proliferate the cytotoxic T cells specific to the peptide in vivo too, therapy and/or prophylaxis of cancers may be achieved by administering the antigen presenting cells. Further, since the T cells which selectively bind the complex between the peptide of the present invention and HLA molecule exhibit cytotoxic activity against the cancer cells expressing YKL-40, therapy and/or prophylaxis of cancers may also be achieved by administering the T cells to a living body. Thus, the present invention also provides a pharmaceutical and a therapeutic and/or prophylactic agent for cancer(s) comprising as an effective ingredient the above-described antigen presenting cell of the present invention; as well as a pharmaceutical and a therapeutic and/or prophylactic agent for cancer(s) comprising as an effective ingredient the above-described T cell of the present invention. Examples of the cancers to be treated include, needless to say, the above-described cancers which may be treated by the therapeutic and/or prophylactic agent for cancer(s) comprising as an effective ingredient the peptide of the present invention.

The antigen presenting cells or T cells to be administered to a living body are preferably those prepared by treating the antigen presenting cells or T cells with the peptide of the present invention as described above, which antigen presenting cells or T cells are collected from the patient to be treated, in order to avoid the immune response in the body that attacks these cells as a foreign body.

The therapeutic and/or prophylactic agent for cancer(s) comprising as an effective ingredient the antigen presenting cells and/or T cells is preferably administered via a parenteral administration route such as intravenous or intraarterial administration. The dose is appropriately selected depending on the symptom, the purpose of administration and the like, and is usually 1 cell to 10,000,000,000,000 cells, preferably 1,000,000 cells to 1,000,000,000 cells. This dose is preferably administered once per several days to several months. The formulation may be, for example, a suspension of the cells in physiological buffered saline, and other anticancer agent(s), cytokine(s) and the like may be co-used. Further, one or more additives well-known in the field of formulation of pharmaceuticals may also be added.

The present invention further provides an antibody whose corresponding antigen is the above-described peptide of the present invention, as well as antigen-binding fragments thereof. The term "antigen-binding fragment" herein means a fragment of an antibody contained in the antibody molecule, such as Fab fragment or F(ab')$_2$ fragment, which has the ability to bind the antigen. Although the antibody may be either a polyclonal antibody or monoclonal antibody, a monoclonal antibody is preferred for immunoassays and the like because the reproducibility is high. Methods for preparing a polyclonal antibody or monoclonal antibody using a peptide as an immunogen are well-known, and may be easily carried out by a conventional method. For example, antibodies to the peptide may be induced by immunizing an animal with the peptide conjugated to a carrier protein such as keyhole limpet hemocyanin (KLH) or casein as an immunogen, together with an adjuvant. A monoclonal antibody whose corresponding antigen is the peptide of the present invention may be obtained by fusing antibody-producing cells such as spleen cells and lymphocytes with myeloma cells to prepare hybridomas, selecting a hybridoma producing the antibody which binds the peptide of the present invention, proliferating the hybridoma, and collecting the antibody from the culture supernatant. The above-described method is a conventional well-known method.

The antibody or the antigen-binding fragment thereof according to the present invention may be used as a reagent for immunoassays for detecting or quantifying the antigen presenting cells which present the peptide of the present invention. Immunoassays per se are well-known in the art, and includes, when classified based on the reaction mode, sandwich method, competition method, agglutination method, Western blot method and the like, and flow cytometry also may be thought as a type of immunoassays. When classified based on the label, immunoassays include radioimmunoassay, fluorescence immunoassay, enzyme immunoassay, biotin immunoassay and the like, and the antibody or the antigen-binding fragment thereof according to the present invention may be applied in any of these immunoassays. When used for detection or quantification of the cells expressing YKL-40, the antibody or antigen-binding fragment thereof according to the present invention functions as a diagnostic agent for a cancer(s). When used as a diagnostic agent for a cancer(s), sandwich ELISA and agglutination method which are simple and do not require a large-scale apparatus are preferred. The above-described peptide of the present invention may also be used as a reagent of immunoassays for detecting or measuring the cells expressing the peptide by competition method.

In an example below, since it was proved that the T cells stimulated with the peptide of the present invention exhibits cytotoxic activity against cancer cells expressing YKL-40, YKL-40 may be administered to a living body as an agent for inducing cancer-specific immunity. Thus, the present invention provides a cancer-specific immunity-inducing agent comprising as an effective ingredient a protein having the amino acid sequence shown in SEQ ID NO:2 or a protein having an immunity-inducing activity, which protein has an amino acid sequence with an identity of not less than 80% to the amino acid sequence shown in SEQ ID NO:2. In this case, the route of administration to a living body, dose of administration, formulation and the like may be the same as the above-described therapeutic and/or prophylactic agent comprising as an effective ingredient the above-described peptide.

The present invention will now be described more concretely by way of examples.

EXAMPLE 1

Induction of CD8-Positive T Cells Reactive with Peptide Epitope Originated from YKL-40

(1) Information about the amino acid sequence of human YKL-40 protein was obtained from GenBank. For the prediction of HLA-A0201-binding motif, the amino acid sequence of human YKL-40 protein was analyzed by a computer program for prediction using a known BIMAS software (available at http://bimas.dcrt.nih.gov/molbio/hla_bind/), and the peptides which were predicted to bind HLA class I molecule were selected.

(2) Peripheral blood was collected from an HLA-A0201-positive healthy donor and overlaid on Lymphocyte separation medium (OrganonpTeknika, Durham, N.C.), and the resultant was centrifuged at 1500 rpm at room temperature for 20 minutes. A PBMC-containing fraction was recovered and washed 3 times (or more) with cold phosphate buffer to obtain peripheral blood mononuclear cells (PB-MCs). The obtained PBMCs were suspended in 20 ml of AIM-V medium (Life Technologies, Inc., Grand Island, N.Y.), and were made to adhere to a culturing flask (Falcon) at 37° C. under 5% $CO_2$ for 2 hours. The cells which were not adhered were used for the preparation of T cells, and the adhered cells were used for the preparation of dendritic cells.

On the other hand, the adhered cells were cultured in AIM-V medium in the presence of L-4 (1000 U/ml) and GM-CSF (1000 U/ml). Six days later, the medium was replaced with AIM-V medium supplemented with IL-4 (1000 U/ml), GM-CSF (1000 U/ml), IL-6 (1000 U/ml, Genzyme, Cambridge, Mass.), IL-1β (10 ng/ml, Genzyme, Cambridge, Mass.) and TNF-α (10 ng/ml, Genzyme, Cambridge, Mass.). The culturing was continued for another 2 days and the obtained population of cells which did not adhere was used as the dendritic cells.

(3) The thus prepared dendritic cells were suspended in AIM-V medium at a cell density of $1 \times 10^6$ cells/ml. Each of the selected peptides was added to a concentration of 10 μg/nl, and the cells were cultured in a 96-well plate at 37° C. under 5% $CO_2$ for 4 hours. After the culturing, the dendritic cells were irradiated with X-ray (3000 rad), washed with AIM-V medium, suspended in AIM-V medium containing 10% human AB serum (Nabi, Miami, Fla.), IL-6 (1000 U/ml) and IL-12 (10 ng/ml, Genzyme, Cambridge, Mass.), placed in the wells of a 24-well plate at a population of $1 \times 10^5$ cells/well. The prepared T cell population was added to the wells at a population of $1 \times 10^6$ cells/well, and the cells were cultured at 37° C. under 5% $CO_2$. Seven days later, each culture supernatant was discarded, and the cells were treated with each of the peptides in the same manner as described above. After irradiation with X-ray, the dendritic cells were suspended in AIM-V medium containing 10% human AB serum (Nabi, Miami, Fla.), IL-7 (10 U/ml Genzyme, Cambridge, Mass.) and IL-2 (10 U/ml, Genzyme, Cambridge, Mass.) (cell density: $1 \times 10^5$ cells/ml), and the cells were placed in the wells of a 24-well plate at a cell population of $1 \times 10^5$ cells/well and further cultured. The same operations were repeated 4 to 6 times at an interval of 7 days, and the induced T cells were recovered. Induction of CD8-positive T cells was confirmed by flow cytometry.

EXAMPLE 2

Figure 5:
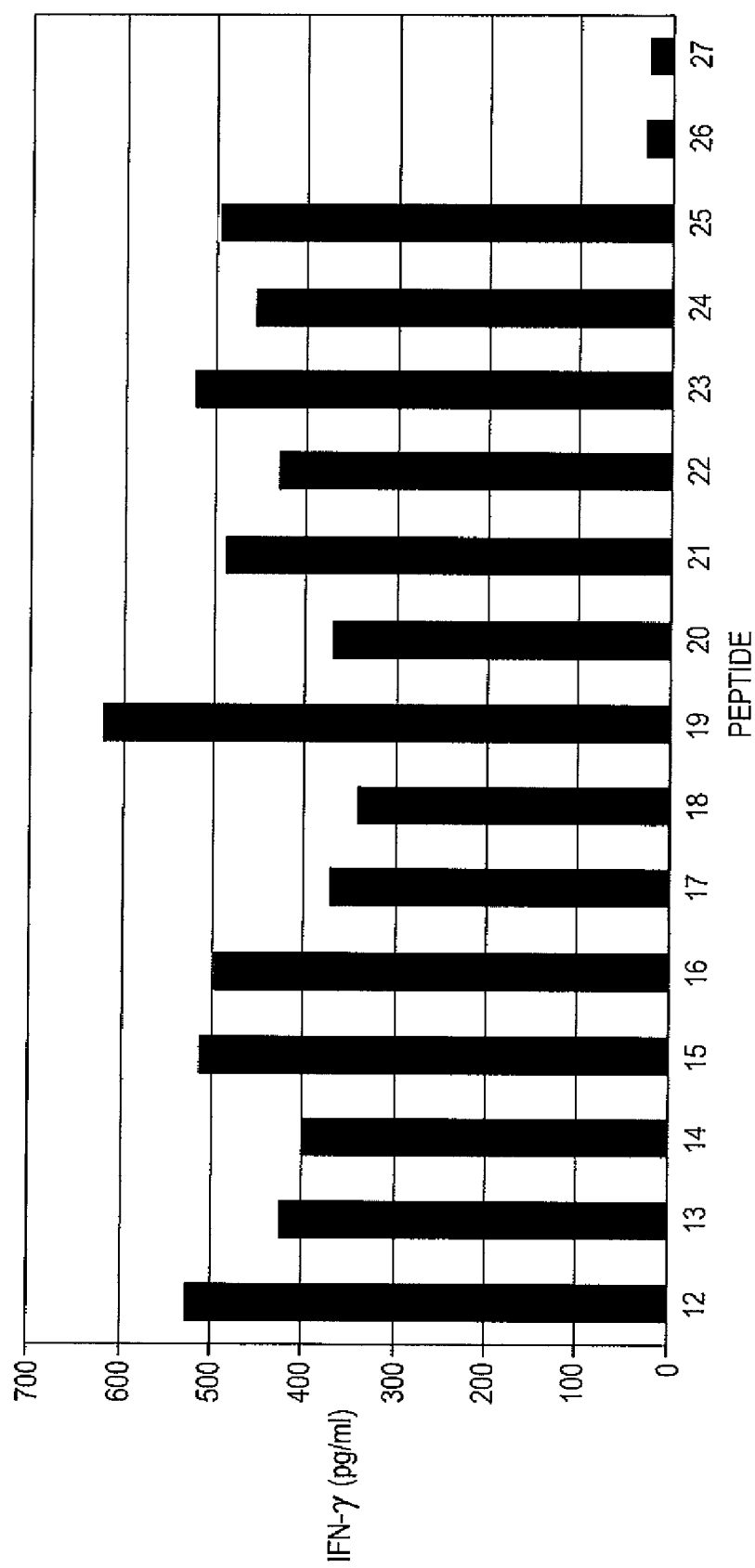
FIG. 5 shows that peptide-specific CD8-positive T cells-recognize the complex between the peptide and HLA-A0201 and produce IFN-γ.

Determination of Antigenic Epitope of Cytotoxic T Cells Originated from YKL-40, Which Stimulates HLA-A0201-Positive CD8-Positive T Cells (1) Among the T cells in the wells, which were stimulated as described above, the T cells stimulated by the peptide having the amino acid sequence shown in SEQ ID NO:3 according to the present invention were confirmed to have proliferated by the counting of the cell number under microscope. To examine the specificity of these T cells to the peptide of SEQ ID NO:3, $5 \times 10^3$ T cells were added to $5 \times 10^4$ T2 cells (reference and source of supply: Salter R D et al., Immunogenetics, 21:235-246 (1985), purchased from ATCC) (cultured in AIM-V medium supplemented with each peptide at a level of 10 μg/ml, at 37° C. under 5% $CO_2$ for 4 hours) pulsed with the peptide, which expressed HLA-A0201 molecules, and the cells were cultured in a 96-well plate in AIM-V medium containing 10% human AB serum for 24 hours. The supernatant after the culturing was recovered and the production amount of IFN-γ was measured by ELISA. As a result, prominent production of IFN-γ was confirmed in the culture supernatant in the well of T2 cells pulsed with the peptide of SEQ ID NO:3, when compared with the culture supernatant of T2 cells which were not pulsed (FIG. 1). Thus, it was proved that the peptide of SEQ ID NO:3 is a T cell epitope peptide which has the ability to specifically stimulate and proliferate the HLA-A0201-positive and CD8-positive T cells. Similarly, 14 types of peptides shown in SEQ ID NO:4 to SEQ ID NO:17, which have an ability to specifically stimulate and proliferate the HLA-A0201-positive and CD8-positive T cells and to induce IFN-γ production (FIG. 5).

In FIG. 1, the result indicated by reference numeral 1 in the ordinate shows the result of the peptide having the amino acid sequence shown in SEQ ID NO:3. The result indicated by reference numeral 2 shows the result of a peptide LQCCSAYKL (SEQ ID NO:19) which is one of the peptides originated from YKL-40 but outside the scope of the present invention (Comparative Example 1). The result indicated by reference numeral 3 shows the result of the case wherein the above-described operations were performed without adding the peptide (Comparative Example 2). In FIG. 5, the results indicated by reference numerals 12 to 25 in the abscissa indicate the results of the peptides having the amino acid sequences shown in SEQ ID NO:4 to SEQ ID NO:17, respectively. The result indicated by reference numeral 26 in the abscissa shows, the result of the peptide of SEQ ID NO:19 which is one of the peptides originated from YKL-40 but outside the scope of the present invention (Comparative Example 3), and the result indicated by reference numeral 27 in the abscissa shows the result of the case wherein the above-described operations were performed without adding the peptide (Comparative Example 4).

Figure 2:
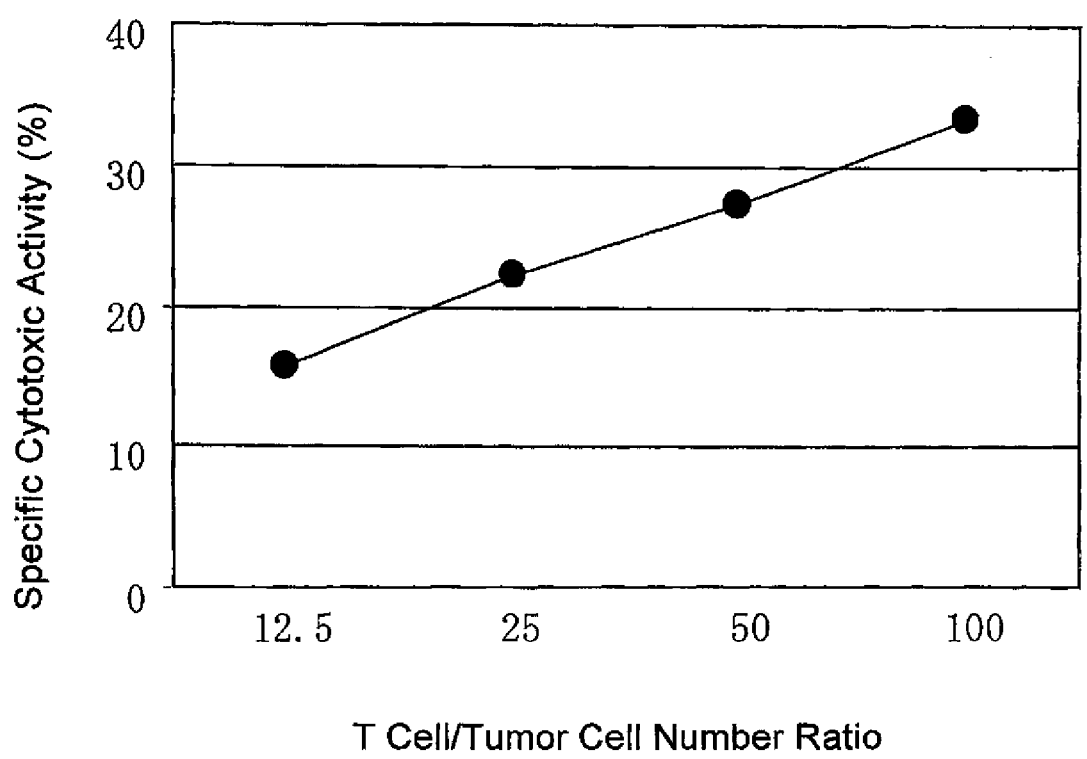
FIG. 2 shows cytotoxic activity of peptide-specific CD8-positive T cells against cancer cells.
Figure 6:
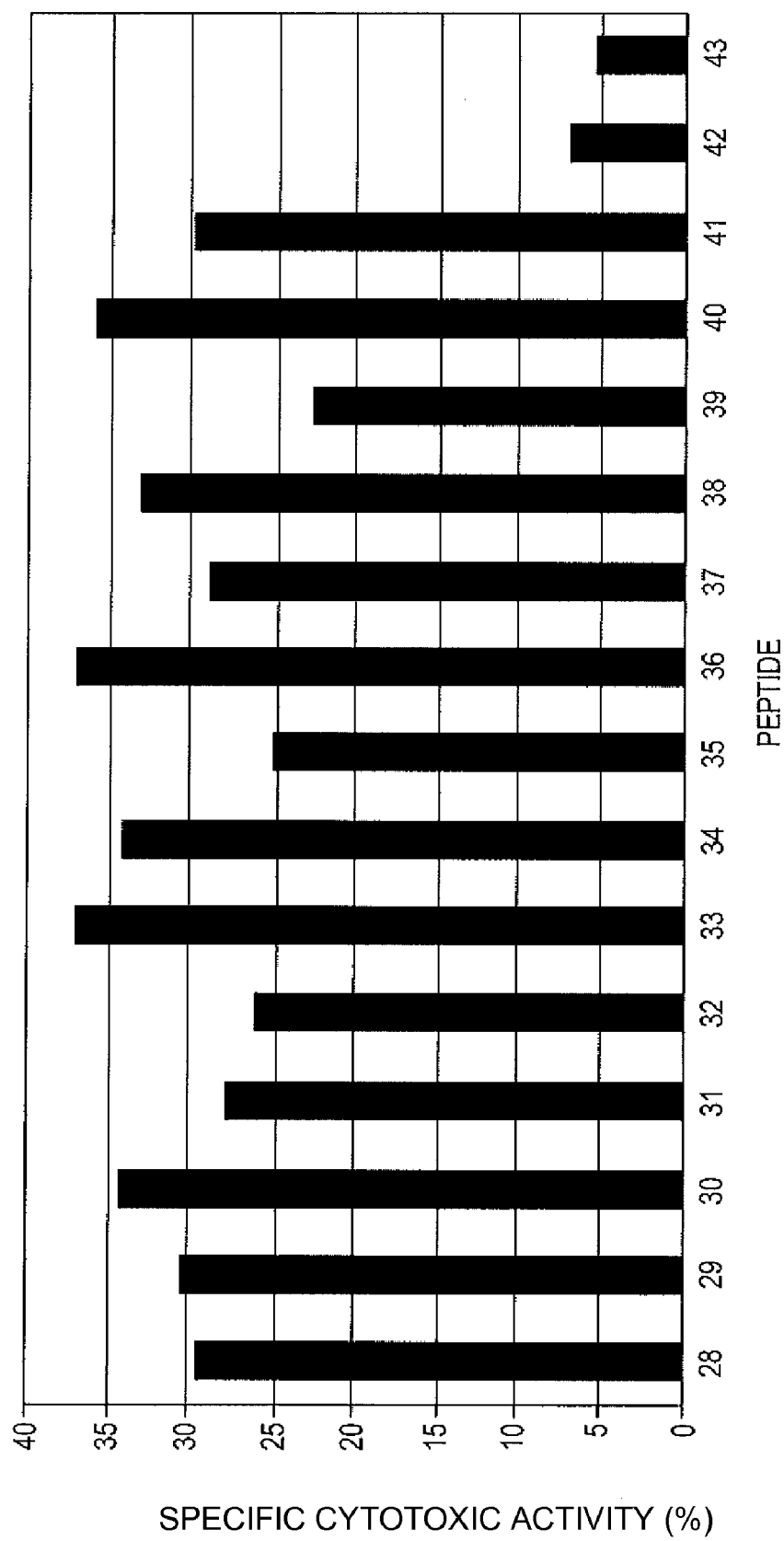
FIG. 6 shows cytotoxic activity of peptide-specific CD8-positive T cells against cancer cells.
Figure 7:
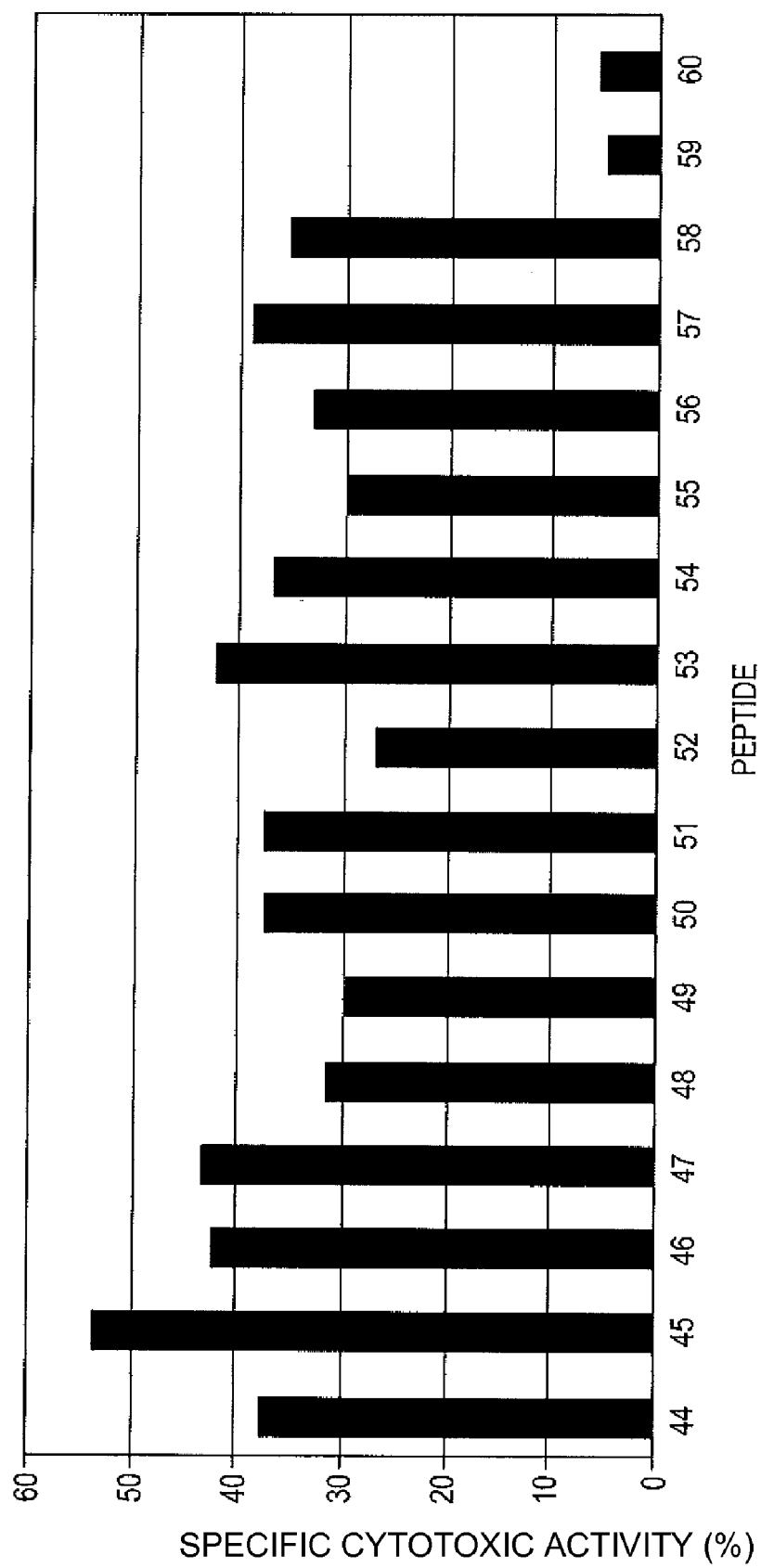
FIG. 7 shows cytotoxic activity of peptide-specific CD8-positive T cells against cancer cells.

(2) Next, whether or not the peptide of SEQ ID NO:3 which is one of the peptides according to the present invention is presented on the HLA-A0201 molecule on tumor cells which are HLA-A0201-positive and express YKL-40, and whether or not the CD8-positive T cells stimulated with this peptide can damage the tumor cells which are HLA-A0201-positive and express YKL-40 were examined. In a 50-ml centrifugal tube, $10^5$ cells of T98G (reference and source of supply: Stein G H et al., J. Cell Physiol., 99: 43-54 (1979), purchased from ATCC) which are malignant brain tumor cell line that had been confirmed to express YKL-40 were collected, and 100 mCi of chromium 51 was added thereto, followed by incubation at 37° C. for 2 hours. The resulting cells were washed 3 times with AIM-V medium containing 10% human AB serum, and then added to the wells of a 96-well V-bottomed plate at a population of $10^3$ cells/well. To the wells, $10^5$, $5 \times 10^4$, $2.5 \times 10^4$ and $1.25 \times 10^4$ HLA-A0201-positive and CD8-positive T cells stimulated with the peptide of SEQ ID NO:3, respectively, suspended in AIM-V medium containing 10% human AB serum, were added, and the cells were cultured at 37° C. under 5% $CO_2$ for 4 hours. After the culturing, the cytotoxic activity of the CD8-positive T cells stimulated with the peptide of SEQ ID NO:3 was calculated by measuring the amount of chromium 51 in the culture supernatant, which was released from the damaged tumor cells. As a result, it was proved that the HLA-A0201-positive and CD8-positive T cells stimulated with the peptide had a cytotoxic activity against T98G (FIG. 2). Thus, it was proved that the peptide of SEQ ID NO:3 which is one of the peptides according to the present invention is presented on the HLA-A0201 molecule on tumor cells which are HLA-A0201-positive and express YKL-40, and that the peptide has an ability to induce the CD8-positive T cells which can damage such tumor cells. Similarly, the HLA-A0201-positive and CD8-positive T cells stimulated with the 14 types of peptides shown in SEQ ID NO:4 to SEQ ID NO:17, respectively, had cytotoxic activity against T98G (FIG. 6). Further, HLA-A0201-positive and CD8-positive T cells stimulated with the 15 types of peptides shown in SEQ ID NO:3 to SEQ ID NO:17, respectively, had cytotoxic activity against U87 MG (Beckman G et al., Hum. Hered., 21:238-241 (1971), purchased from ATCC) which is another malignant brain tumor cell line which had been confirmed to express YKL-40 thereon (FIG. 7).

The cytotoxic activity was determined by, as described above, mixing $10^5$ CD8-positive T cells stimulated and induced with each of the peptides of the present invention and $10^3$ malignant brain tumor cell line T98G or U87 MG which were made to incorporate chromium 51; culturing the resultant for 4 hours; measuring the amount of chromium 51 released to the culture medium after the culturing; and calculating the cytotoxic activity according to the following equation*:

*Equation: Cytotoxic Activity (%)=(Amount of chromium 51 released from T98G or U87 MG when CD8-positive T cells were added)/(Amount of chromium 51 released from the target cells to which 1N hydrochloric acid was added)×100

In FIG. 6, the results indicated by reference numerals 28 to 41 in the abscissa show the results of the peptides shown in SEQ ID NO:4 to SEQ ID NO:17, respectively. Further, the result indicated by reference numeral 42 in the abscissa shows the result of the peptide of SEQ ID NO:19 which is one of the peptides originated from YKL-40 but outside the scope of the present invention (Comparative Example 5), and the result indicated by reference numeral 43 in the abscissa shows the result of the case wherein the above-described operations were performed without adding the peptide (Comparative Example 6). In FIG. 7, the results indicated by reference numerals 44 to 58 in the abscissa show the results of the peptides shown in SEQ ID NO:3 to SEQ ID NO:17, respectively. Further, the result indicated by reference numeral 59 in the abscissa shows the result of the peptide of SEQ ID NO:19 which is one of the peptides originated from YKL-40 but outside the scope of the present invention (Comparative Example 7), and the result indicated by reference numeral 60 in the abscissa shows the result of the case wherein the above-described operations were performed without adding the peptide (Comparative Example 8).

EXAMPLE 3

Induction of CD4-Positive T Cells Reactive with Peptide Epitope Originated from YKL-40

(1) For the prediction of CD4-positive T cell antigen epitope, the amino acid sequence of human YKL-40 protein was analyzed by 3 computer programs for prediction, that is, SYFPEITHI algorithm (Rammensee and 4 others, "Immunogenetics", 1999, vol. 50, p. 213-219); ProPred algorithm, Singh and another, "Bioinformatics", 2001, Vol. 17, p. 1236-1237); and RANKPEP algorithm (Reche and 2 others, "Human Immunology", and the peptides which were predicted to bind HLA class II molecule were selected.

(2) Peripheral blood was collected from an HLA-DRB1*04-positive healthy donor and overlaid on Lymphocyte separation medium (OrganonpTeknika, Durham, N.C.), and the resultant was centrifuged at 1500 rpm at room temperature for 20 minutes. A PBMC-containing fraction was recovered and washed 3 times (or more) with cold phosphate buffer to obtain peripheral blood mononuclear cells (PBMCs). The obtained PBMCs were suspended in 20 ml of AIM-V medium (Life Technologies, Inc., Grand Island, N.Y.), and were made to adhere to a culturing flask (Falcon) at 37° C. under 5% $CO_2$ for 2 hours. The cells which were not adhered were used for the preparation of T cells, and the adhered cells were used for the preparation of dendritic cells.

On the other hand, the adhered cells were cultured in AIM-V medium in the presence of IL-4 (1000 U/ml) and GM-CSF (1000 U/ml). Six days later, the medium was replaced with AIM-V medium supplemented with IL-4 (1000 U/ml), GM-CSF (1000 U/ml), IL-6 (1000 U/ml, Genzyme, Cambridge, Mass.), IL-1β (10 ng/ml, Genzyme, Cambridge, Mass.) and TNF-α (10 ng/ml, Genzyme, Cambridge, Mass.). The culturing was continued for another 2 days and the obtained population of cells which did not adhere was used as the dendritic cells.

(3) The thus prepared dendritic cells were suspended in AIM-V medium at a cell density of $1\times10^6$ cells/ml. Each of the selected peptides was added to a concentration of 10 mg/ml, and the cells were cultured in a 96-well plate at 37° C., under 5% $CO_2$ for 4 hours. After the culturing, the cells were irradiated with X-ray (3000 rad), washed with AIM-V medium, suspended in AIM-V medium containing 10% human AB serum (Nabi, Miami, Fla.), IL-6 (1000 U/ml) and IL-12 (10 ng/ml, Genzyme, Cambridge, Mass.), and placed in the wells of a 24-well plate at a population of $1\times10^5$ cells/well. The prepared T cell population was added to the wells at a population of $1\times10^6$ cells/well, and the cells were cultured at 37° C. under 5% $CO_2$. Seven days later, each culture supernatant was discarded, and the cells were treated with each of the peptides in the same manner as described above. After irradiation with X-ray, the dendritic cells were suspended in AIM-V medium containing 10% human AB serum (Nabi, Miami, Fla.) and IL-2 (10 U/ml, Genzyme, Cambridge, Mass.), and the cells were placed in the wells of a 24-well plate at a cell population of $1\times10^5$ cells/well and further cultured. The same operations were repeated 4 to 6 times at an interval of 7 days, and the stimulated T cells were recovered. Induction of CD4-positive T cells was confirmed by flow cytometry.

EXAMPLE 4

Determination of Antigenic Epitope of Helper T Cells, Originated from YKL-40, Which Stimulates HLA-DRB1*04-Positive and CD4-Positive T Cells (1) Among the T cells in the wells, which were stimulated as described above, the T cells stimulated by the peptide having the amino acid sequence shown in SEQ ID NO:18 according to the present invention were confirmed to have proliferated by the counting of the cell number under microscope. To examine the specificity of these T cells to the peptide of SEQ ID NO:18, $5\times10^3$ CD4-positive T cells were added to $5\times10^4$ T2DR4 cells expressing HLA-DRB1*04 molecules pulsed with the peptide (the peptide was added to AIM-V medium at a concentration of 10 µg/ml, and the cells were cultured at 37° C. under 5% $CO_2$ for 4 hours), and the cells were cultured in a 96-well plate in AIM-V medium containing 10% human AB serum for 24 hours. The supernatant after the culturing was recovered and the production amount of IFN-γ was measured by ELISA. As a result, not less than 1000 pg/ml of IFN-γ was produced in the culture supernatant in the well of T2DR4 cells pulsed with the peptide of SEQ ID NO:18 (FIG. 3).

Figure 3:
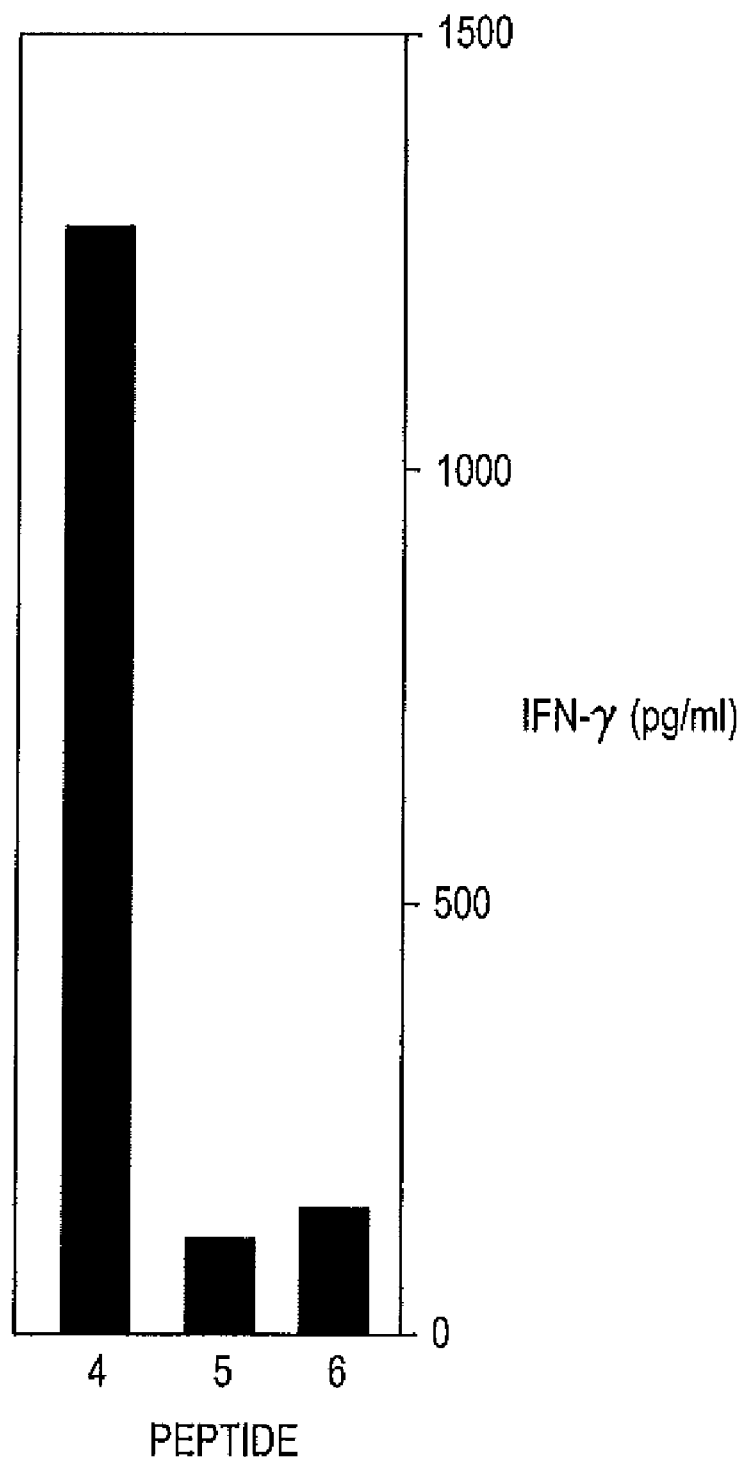
FIG. 3 shows that peptide-specific CD4-positive T cells recognize the complex between the peptide and HLA-DRB1*04 and produce IFN-γ.

On the other hand, in the culture supernatants in the wells of T2DR4 cells pulsed with another peptide and of T2DR4 cells which were not pulsed, respectively, production of IFN-γ was hardly observed (FIG. 3). Thus, it was proved that the peptide of SEQ ID NO:18 is a T cell epitope peptide which has the ability to specifically stimulate and proliferate the HLA-DRB1*04-positive and CD8-positive T cells.

In FIG. 3, the result indicated by reference numeral 4 in the ordinate shows the result of the peptide having the amino acid sequence shown in SEQ ID NO:18. Further, the result indicated by reference numeral 5 shows the result of the peptide of SEQ ID NO:19 which is one of the peptides originated from YKL-40 but outside the scope of the present invention (Comparative Example 7). The result indicated by reference numeral 6 shows the result of the case wherein the above-described operations were performed without adding the peptide (Comparative Example 8).

Figure 4:
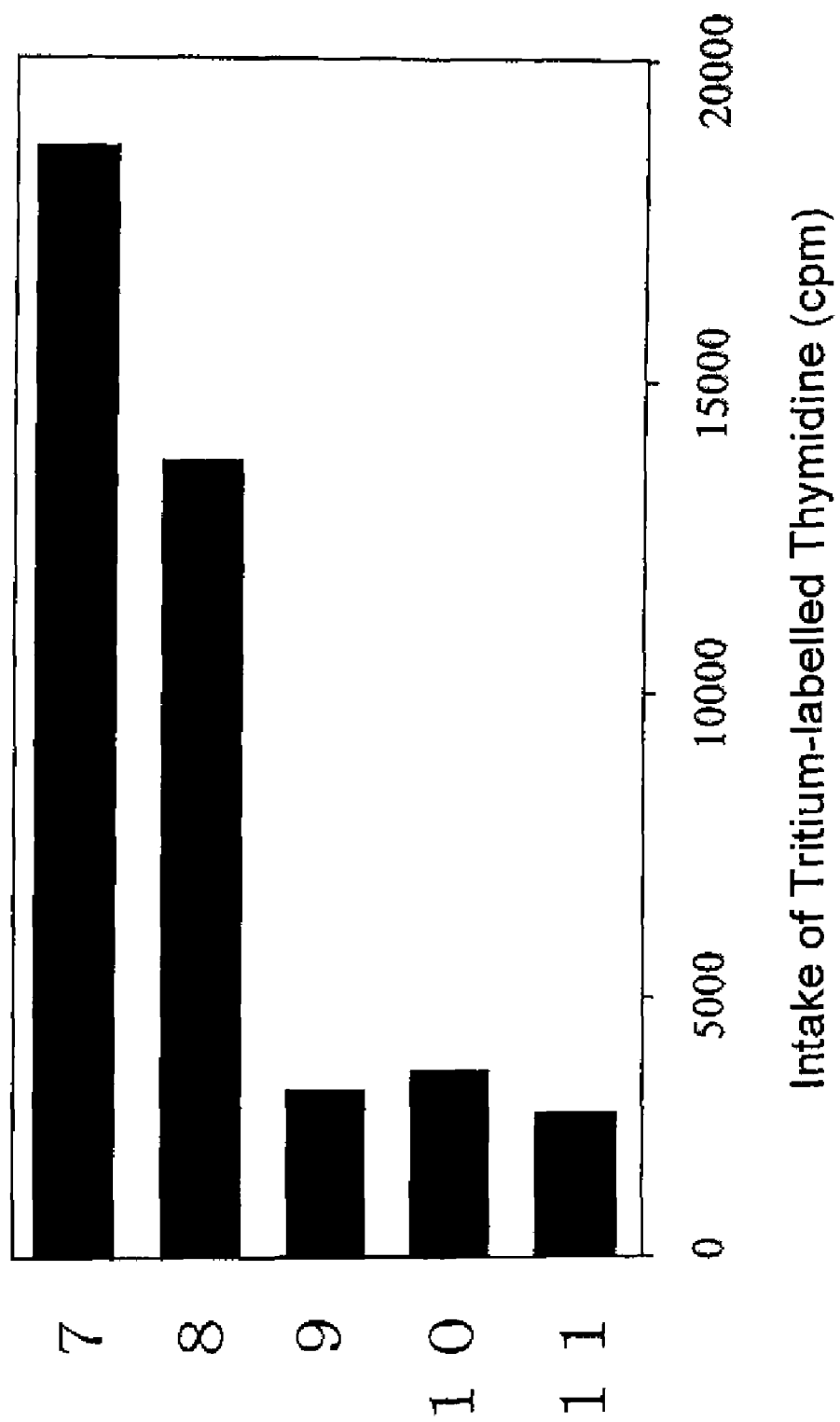
FIG. 4 shows that peptide-specific CD4-positive T cells react with dendritic cells which englobed lysate of cancer cells, and proliferate.

(2) Next, whether or not this peptide having the ability to stimulate and proliferate HLA-DRB1*04-positive cells is the epitope presented on HLA-DR when YKL-40 protein is naturally processed in the antigen presenting cells was examined. Lysate of T98G which is a malignant brain tumor cell line which had been confirmed to express YKL-40 was added to immature dendritic cells and the cells were made to digest the lysate, thereby maturating the dendritic cells. Thereafter, whether or not the T cells stimulated with the peptide are stimulated with these dendritic cells was examined. A pellet of $1.5 \times 10^6$ T98G cells were subjected to freeze-thaw cycle 7 times using liquid nitrogen and hot water bath to prepare a cell lysate. On the other hand, peripheral blood was collected from an HLA-DRB1*04-positive healthy donor, and overlaid on Lymphocyte separation medium, followed by centrifuging the resultant at 1500 rpm at room temperature for 20 minutes. An interface containing PBMCs was collected, and washed 3 times (or more) with cold phosphate buffer to obtain PBMCs. The obtained PBMCs were suspended in 20 ml of AIM-V medium, and then made to adhere in a culturing flask (Falcon) at 37° C. under 5% $CO_2$ for 2 hours. The adhered cells were cultured in AIM-V medium in the presence of IL-4 (1000 U/ml) and GM-CSF (1000 U/ml) for 6 days to prepare immature dendritic cells. Each cell lysate prepared was added to $5 \times 10^5$ immature dendritic cells and the cells were cultured in AIM-V medium supplemented with IL-4 (1000 U/ml), GM-CSF (1000 U/ml), IL-6 (1000 U/ml), IL-1β (10 ng/ml) and TNF-α (10 ng/ml) at 37° C. under 5% $CO_2$ for 2 days. In parallel, immature dendritic cells to which the peptide of SEQ ID NO:18 was added, and immature dendritic cells to which cell lysate (prepared from a cell pellet of $1.5 \times 10^6$ cells) of PBMCs was added were prepared, respectively, and the cells were cultured in AIM-V medium supplemented with IL-4 (1000 U/ml), GM-CSF (1000 U/ml), IL-6 (1000 U/ml), IL-1β (10 ng/ml) and TNF-α (10 ng/ml) at 37° C. under 5% $CO_2$ for 2 days. The dendritic cells after the culturing were irradiated with X-ray (3000 rad) and washed with AIM-V medium. The cells were then suspended in AIM-V medium containing 10% human AB serum, and the suspension was added to the wells of a 96-well plate at a population of $3.3 \times 10^4$ cells/well. To the cells, $5 \times 10^4$ T cells stimulated with YKL peptide were added, and the cells were cultured at 37° C. under 5% $CO_2$ for 72 hours. To each culture medium, 1 mCi tritium-labelled thymidine was added at 48 hours after the beginning of the culturing. After the culturing, cells were collected on a glass filter paper with a cell harvester, and the intake of the tritium-labelled thymidine was measured with a liquid scintillation counter. As a result, as shown in FIG. 4, it was confirmed that the T cells stimulated with the peptide of SEQ ID NO:18 were proliferated by the stimulation by the dendritic cells to which the lysate of T98G cells was added. Further, since these reactions were inhibited by the addition of an anti-HLA-DR neutralizing antibody, it was proved that the peptide of SEQ ID NO:18 is an epitope resulting from natural processing of YKL-40 protein in antigen presenting cells and presented on HLA-DR.

In FIG. 4, the result indicated by reference numeral 7 in the ordinate shows the intake of tritium-labelled thymidine by the CD4-positive T cells obtained by culturing a mixture of HLA-DRB1*04-positive dendritic cells pulsed with the peptide of SEQ ID NO:18 of the present invention irradiated with X-ray and HLA-DRB1*04-positive and CD4-positive T cells stimulated and induced by the peptide in AIM-V medium containing 10% human AB serum for 48 hours, then further adding tritium-labelled thymidine, and then culturing the cells for another 24 hours. The result indicated by reference numeral 8 shows the intake of tritium-labelled thymidine by the CD4-positive T cells obtained by culturing a mixture of HLA-DRB1*04-positive dendritic cells which were made to incorporate the lysate of the malignant brain tumor cell line T98G and irradiated with X-ray and HLA-DRB1*04-positive and CD4-positive T cells stimulated and induced by the peptide of SEQ ID NO:18 according to the present invention in AIM-V medium containing 10% human AB serum for 48 hours, then further adding tritium-labelled thymidine, and then culturing the cells for another 24 hours. The result indicated by reference numeral 9 shows the intake of tritium-labelled thymidine by the CD4-positive T cells obtained by culturing a mixture of HLA-DRB1*04-positive dendritic cells which were made to incorporate the lysate of the malignant brain tumor cell line T98G and irradiated with X-ray and HLA-DRB1*04-positive and CD4-positive T cells stimulated and induced by the peptide of SEQ ID NO:18 according to the present invention in AIM-V medium containing 10% human AB serum and an anti-HLA-DR antibody for 48 hours, then further adding tritium-labelled thymidine, and then culturing the cells for another 24 hours. The result indicated by reference numeral 10 shows the intake of tritium-labelled thymidine by the CD4-positive T cells obtained by culturing a mixture of HLA-DRB1*04-positive dendritic cells which were made to incorporate the lysate of peripheral blood mononuclear cells separated from a HLA-DRB1*04-positive healthy donor and irradiated with X-ray and HLA-DRB1*04-positive and CD4-positive T cells stimulated and induced by the peptide of SEQ ID NO: 18 according to the present invention in AIM-V medium containing 10% human AB serum for 48 hours, then further adding tritium-labelled thymidine, and then culturing the cells for another 24 hours. The result indicated by reference numeral 11 shows the intake of tritium-labelled thymidine by the CD4-positive T cells obtained by culturing a mixture of HLA-DRB1*04-positive dendritic cells which were irradiated with X-ray and HLA-DRB1*04-positive and CD4-positive T cells stimulated and induced by the peptide of SEQ ID NO:18 according to the present invention in AIM-V medium containing 10% human AB serum for 48 hours, then further adding tritium-labelled thymidine, and then culturing the cells for another 24 hours.

INDUSTRIAL AVAILABILITY

The peptides according to the present invention are useful as an effective ingredient of a therapeutic and/or prophylactic agent for cancer(s), and are useful for inducing antigen presenting cells or T cells which may be used as a therapeutic and/or prophylactic agent for cancer(s).

The invention claimed is:

1. A peptide having 7 to 15 amino acids, wherein said peptide has 7 to 10 consecutive amino acids from a region of aa202-211 in SEQ ID NO: 2 or a peptide having 7 to 10 amino acid residues of region of aa202-211 in SEQ ID NO: 2 or a peptide having 8 to 11 amino acid residues, wherein 8 to 10 amino acid residues are from the region of aa202-211 in SEQ ID NO: 2 and further comprising an additional amino acid addition, or a peptide having an identity of at least 90% to any one of said peptides, which peptide has a tumor immunity-inducing activity.

2. The peptide according to claim 1, which is said peptide having 7 to 15 amino acids, wherein said peptide has 7 to 10 consecutive amino acids from a region of aa202-211 in SEQ ID NO: 2 said peptide having 8 to 11 amino acid residues, wherein 8 to 10 amino acid residues are from the region of aa202-211 in SEQ ID NO: 2 and further comprising an additional amino acid addition, which peptide has a tumor immunity-inducing activity.

3. The peptide according to claim 1, which is an amino acid sequence shown in SEQ ID NO:4.

4. A pharmaceutical comprising as an effective ingredient said peptide according to claim 1.

5. A therapeutic cancer agent comprising as an effective ingredient said peptide according to claim 1.

6. A method for treating cancer comprising administering an effective amount of said peptide according to claim 1 to an individual in need thereof.

7. An agent for treating antigen presenting cells, said agent comprising said peptide according to claim 1.

8. A cancer-specific immunity-inducing agent comprising as an effective ingredient a protein having the amino acid sequence shown in SEQ ID NO:2 or a protein having a tumor immunity-inducing activity, which protein has an amino acid sequence with an identity of at least 99% to said amino acid sequence shown in SEQ ID NO:2.

9. A peptide consisting of 7 to 15 amino acids, wherein said peptide has 7 to 10 consecutive amino acids from a region of aa202-211 in SEQ ID NO: 2 selected from:

(a) a peptide of 7 to 10 amino acid residues of region aa202-211 in SEQ ID NO: 2; or (b) a peptide of 8 to 11 amino acid residues, wherein 8 to 10 amino acid residues are from the region aa202-211 in SEQ ID NO: 2 and further comprising one amino acid addition; or (c) a peptide having at least 90% identity to the peptide of (a) or (b); which peptide has a tumor-immunity inducing activity.

* * * * *